US007869010B2

(12) United States Patent
Coric

(10) Patent No.: US 7,869,010 B2
(45) Date of Patent: Jan. 11, 2011

(54) METHOD FOR EVALUATING PURITY AND CONCENTRATION OF OILS AND FATTY ACID COMPOSITIONS

(75) Inventor: Vladimir Coric, Madison, CT (US)

(73) Assignee: Cenestra LLC, New Haven, CT (US)

(*) Notice: Subject to any disclaimer, the term of this patent is extended or adjusted under 35 U.S.C. 154(b) by 197 days.

(21) Appl. No.: 12/359,034

(22) Filed: Jan. 23, 2009

(65) Prior Publication Data
US 2009/0244517 A1  Oct. 1, 2009

(51) Int. Cl.
*G01N 33/28* (2006.01)
(52) U.S. Cl. ......................................................... 356/70
(58) Field of Classification Search .................... 356/70
See application file for complete search history.

(56) References Cited

U.S. PATENT DOCUMENTS 5,311,274 A * 5/1994 Cole, Jr. ..................... 356/133

* cited by examiner

*Primary Examiner*—Roy Punnoose
(74) *Attorney, Agent, or Firm*—Hogan Lovells US LLP

(57) ABSTRACT

Methods for evaluation of fish oil, oils, omega-3 fatty acid compositions, and dietary supplements containing omega-3 essential fatty acids and other fats are provided herein. The relative purity and/or concentration of oil-containing aliquots can be determined by cooling approximately equal volumes of two or more aliquots to a temperature near or below 0 degrees Celsius. When cooled, the most opaque aliquots are the least pure. The invention also provide a method for determining whether an omega-3 fatty acid supplement is greater than 90% pure, which includes cooling the supplement to less than 0 degrees Celsius and a determining that the supplement is 90% pure if its appearance is essentially unchanged from its appearance and room temperature.

8 Claims, 1 Drawing Sheet

Photograph of two different Omega-3 samples, frozen. The sample on the right is higher purity and remains clear when frozen, while the sample on the left is lower purity and is opaque when frozen.

Photograph of two different Omega-3 samples, frozen. The sample on the right is higher purity and remains clear when frozen, while the sample on the left is lower purity and is opaque when frozen.

METHOD FOR EVALUATING PURITY AND CONCENTRATION OF OILS AND FATTY ACID COMPOSITIONS

FIELD OF THE INVENTION

Methods for evaluation of fish oil, oils, omega-3 fatty acid compositions, and dietary supplements containing omega-3 essential fatty acids and other fats are provided herein.

BACKGROUND OF THE INVENTION

Dietary supplements and other products containing oils and fatty acids, for example omega-3 fatty acid supplements, vary significantly in concentration and purity. However, high concentration/high purity products are of indistinguishable to the naked eye from lower purity/lower concentration products at or above ambient room temperature. There exists a need for a simple method for a simple method for distinguishing low purity/low concentration oil-containing products from high purity/high concentration supplements or other oil containing products.

SUMMARY OF THE INVENTION

The invention includes a method of determining the relative purity of an oil aliquot comprising cooling a first oil aliquot; cooling a second oil aliquot; wherein the volumes of the first and second oil aliquots are approximately the same, and wherein the cooling is cooling sufficient to reduce the temperature of the first and second oil aliquots to less than 15 degrees Celsius; and comparing the opacity of the first oil aliquot and the opacity of the second oil aliquot and determining that the purity of the less opaque oil aliquot is greater than the purity of the more opaque oil aliquot.

The invention also includes a method for determining that an omega 3 fatty acid aliquot is greater than 90 percent pure omega 3 fatty acid comprising cooling the aliquot to a temperature of less than 0 degrees Celsius; observing whether the aliquot is clear at the temperature less than 0 degrees Celsius; and determining the aliquot is greater than 90 percent pure if it is clear at the temperature less than 0 degrees Celsius.

DETAILED DESCRIPTION

Figure 1:
FIG. 1. Photograph of two different Omega-3 samples, frozen. The higher purity sample remains clear.

The present invention provides a method that can quickly distinguish a less pure and/or less concentrated oil aliquot from a more pure and/or more concentrated oil aliquot. The method includes (i) placing an oil aliquot either in a container (such as, but not limited to a jar, flask, beaker, vial, or tube) or formulated as a gel tab or soft gel in the freezer for a period of time sufficient to lower the temperature of the oil aliquot (ii) determining the opacity of the oil aliquot, and (iii) determining that an oil aliquot which remains clear at the lower temperature is pure and/or concentrated. In some embodiments the invention includes reducing the temperature of the oil aliquot to less than 15 degrees Celsius, but more preferably the temperature of the oil aliquot should be reduced to less than 0 degrees Celsius, and in some instances the temperature should be reduced to between about −40 degrees Celsius and −85 degrees Celsius. The invention may be used to determine the relative purity of oil aliquots. When two oil aliquots having approximately the same volume are subjected to the same chilling conditions the aliquot that is more opaque at reduced temperature is less pure/less concentrated than the oil aliquot that is less opaque. The optimal cooling time for the oil aliquot may be determined empirically by recording the appearance of a oil aliquot with known impurities at time points until the oil aliquot can easily be determined to be opaque by visual examination.

In a preferred embodiment the oil aliquot is an omega-3 fatty acid composition. The method is used to determine the relative purity of omega-3 fatty acid samples by cooling a first omega 3 fatty acid samples; cooling a second omega 3 fatty acid sample; wherein the volumes of the first and second fatty acid samples are approximately the same, and wherein the cooling is cooling sufficient to reduce the temperature of the first and second oil aliquots to less than 15 degrees Celsius; and comparing the opacity of the first omega-3 sample and the opacity of the omega-3 sample and determining that the purity and/or concentration of the less opaque omega-3 fatty acid sample is greater than the purity/concentration of the more opaque sample While not being bound by any particular theory, the inventor believes that the test works because it is able to distinguish saturated fats from unsaturated fats. Less purified oil aliquots appear cloudy, because the likely impurities in an oil samples are saturated fats Saturated fats form a semi-solid or solid at room temperature or below. Solid saturated fats are grey, significantly discolored or opaque at lower temperatures. The test also works because omega 3 essential fatty acids are polyunsaturated fats and are liquid when stored at room temperature or below.

The invention can easily distinguish high purity omega-3 fatty acid supplements from less pure supplements, containing greater amounts of saturated fats. Using this test, less pure fish oil supplements, which contain other saturated fats and have a solid or semi-solid appearance at reduced temperature, are easily distinguished from high purity omega-3 fatty acid supplements, which remain liquid even below room temperature, at 0 degrees Celsius or less. When frozen, aliquots that are greater than 90% pure omega fatty acids, maintain the same or similar appearance to that at room temperature. Lower purity omega 3 fatty acid supplements look cloudy and become less transparent as their temperature decreases.

What is claimed is:

1. A method of determining the relative purity of an oil aliquot comprising
   cooling a first oil aliquot;
   cooling a second oil aliquot;
   wherein the volumes of the first and second oil aliquots are approximately the same, and wherein the cooling reduces the temperature of the first and second oil aliquots to less than 15 degrees Celsius; and
   comparing the opacity of the first oil aliquot and the opacity of the second oil aliquot and determining that the purity of the less opaque oil aliquot is greater than the purity of the more opaque oil aliquot.

2. The method of claim 1, wherein the first and second oil aliquots are oil-containing unit dosage forms.

3. The method of claim 2, wherein the unit dosage forms are either both gel tabs or soft capsules.

4. The method of claim 2, wherein the unit dosage forms are both unit dosage form of the same nutritional supplement.

5. The method of claim 4, wherein the unit the nutritional supplement is an omega 3 fatty acid supplement.

6. The method of claim 5, wherein the unit dosage forms are both soft gel capsules.

7. The method of claim 1, wherein the cooling is cooling sufficient to reduce the temperature of the first and second oil aliquots to less than 0 degrees Celsius.

8. The method of claim 1, wherein the cooling is sufficient to reduce the temperature of the first and second oil aliquots to a temperature between about negative 45 degrees Celsius and about negative 85 degrees Celsius.

* * * * *